US012408872B2

(12) United States Patent
Chahine et al.

(10) Patent No.: US 12,408,872 B2
(45) Date of Patent: Sep. 9, 2025

(54) SYSTEMS AND METHODS OF PROVIDING NETWORKS BASED ON TEXTILES

(71) Applicant: MYANT INC., Toronto (CA)

(72) Inventors: Tony Chahine, Toronto (CA); Milad Alizadeh-Meghrazi, Toronto (CA); Godfried Gysbrecht Edelman, Toronto (CA)

(*) Notice: Subject to any disclaimer, the term of this patent is extended or adjusted under 35 U.S.C. 154(b) by 338 days.

(21) Appl. No.: 17/781,021

(22) PCT Filed: Dec. 1, 2020

(86) PCT No.: PCT/CA2020/051643
§ 371 (c)(1),
(2) Date: May 30, 2022

(87) PCT Pub. No.: WO2021/108900
PCT Pub. Date: Jun. 10, 2021

(65) Prior Publication Data
US 2023/0038068 A1 Feb. 9, 2023

Related U.S. Application Data

(60) Provisional application No. 62/942,962, filed on Dec. 3, 2019.

(51) Int. Cl.
A61B 5/00 (2006.01)
A47B 83/00 (2006.01)
G01D 21/00 (2006.01)
H02J 50/10 (2016.01)

(52) U.S. Cl.
CPC .......... A61B 5/6887 (2013.01); A47B 83/001 (2013.01); H02J 50/10 (2016.02)

(58) Field of Classification Search
CPC ............ A47B 83/001; A61B 2562/125; A61B 5/6804; A61B 5/6887; G01D 21/00; H02J 2310/23; H02J 50/10
See application file for complete search history.

(56) References Cited

U.S. PATENT DOCUMENTS 10,459,611 B1* 10/2019 Sculley ................ A47B 83/001
2014/0359722 A1* 12/2014 Schultz ............... H04L 63/0861
726/5
2015/0282766 A1* 10/2015 Cole ..................... A61B 5/1123
702/139
2016/0163302 A1* 6/2016 Klabunde .............. H05B 47/12
381/56

OTHER PUBLICATIONS

World Intellectual Property Organization, International Search Report and Written Opinion, date of mailing: Feb. 11, 2021 for PCT Application No. PCT/CA2020/051643.

* cited by examiner

Primary Examiner — Benjamin J Klein
Assistant Examiner — Vynn V Huh
(74) Attorney, Agent, or Firm — Norton Rose Fulbright Canada LLP

(57) ABSTRACT

Systems and methods described herein include disparate textiles integrated with fixtures or objects within a workspace. The respective disparate textiles may be interconnected via electrical interconnection busses and may include electrical, mechanical, or electro-mechanical structures for sensing data associated with workspace users. The systems may provide, based on the sensed data, actuator output to one or more disparate textiles for personalizing or altering the workspace environment.

14 Claims, 5 Drawing Sheets

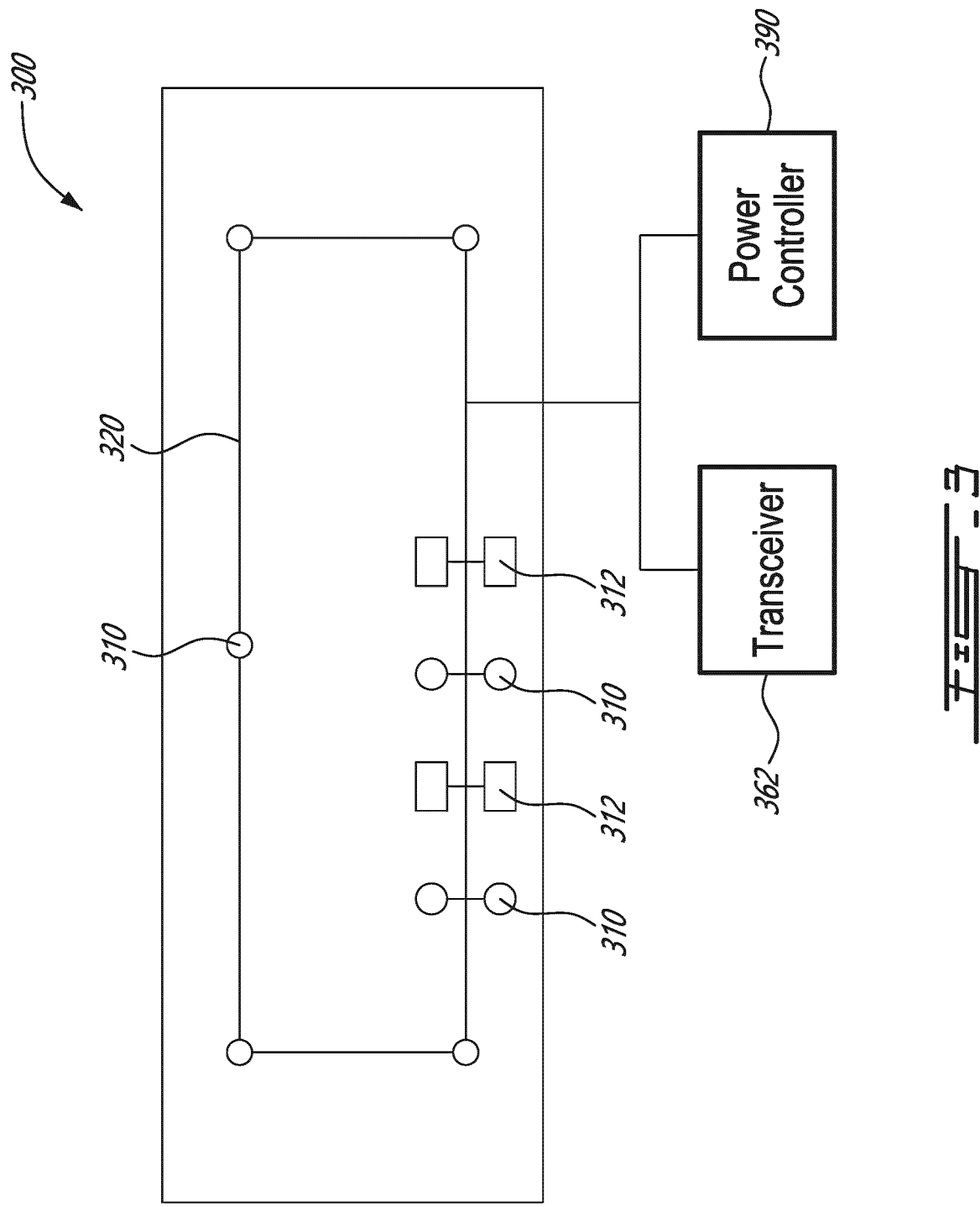

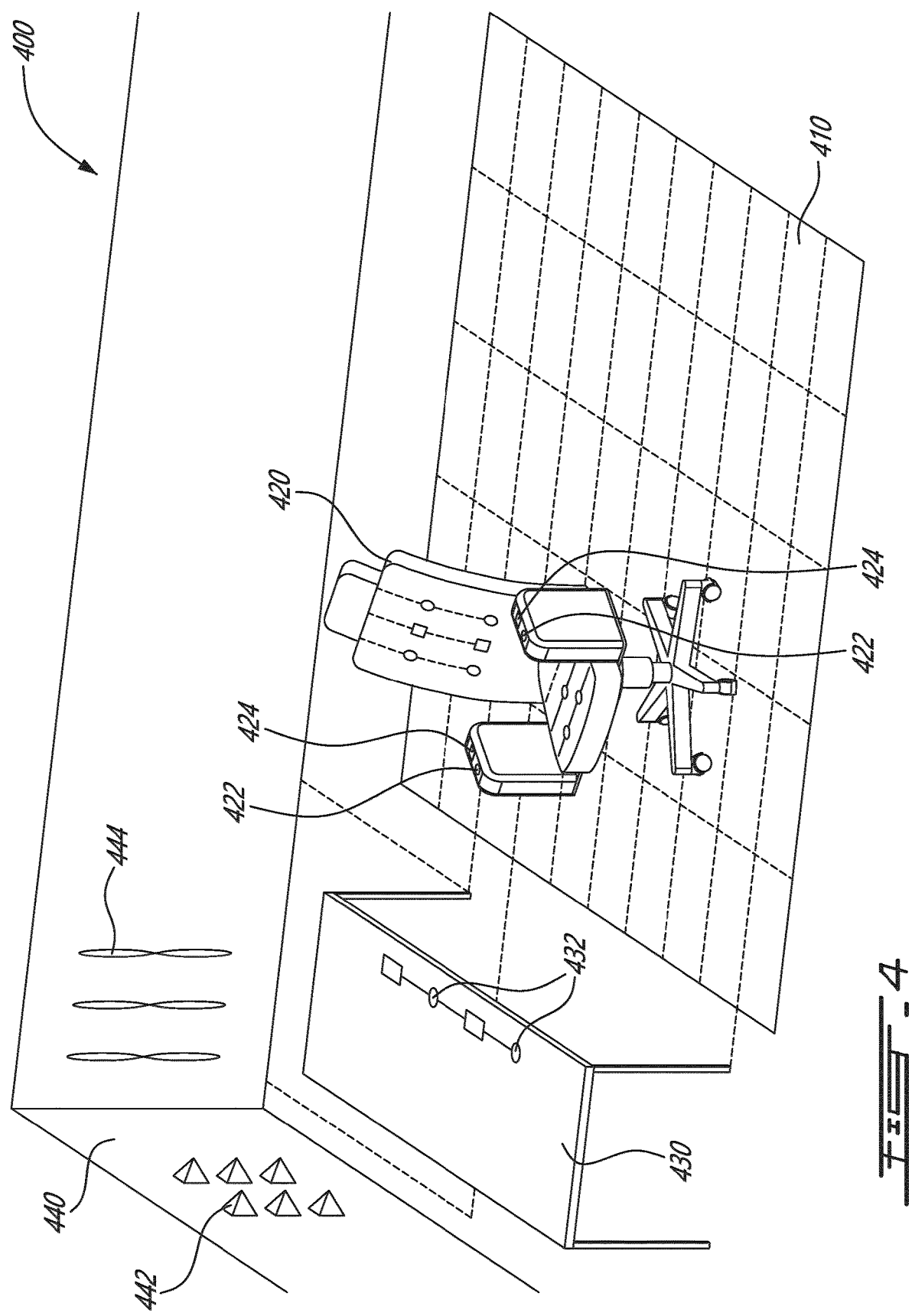

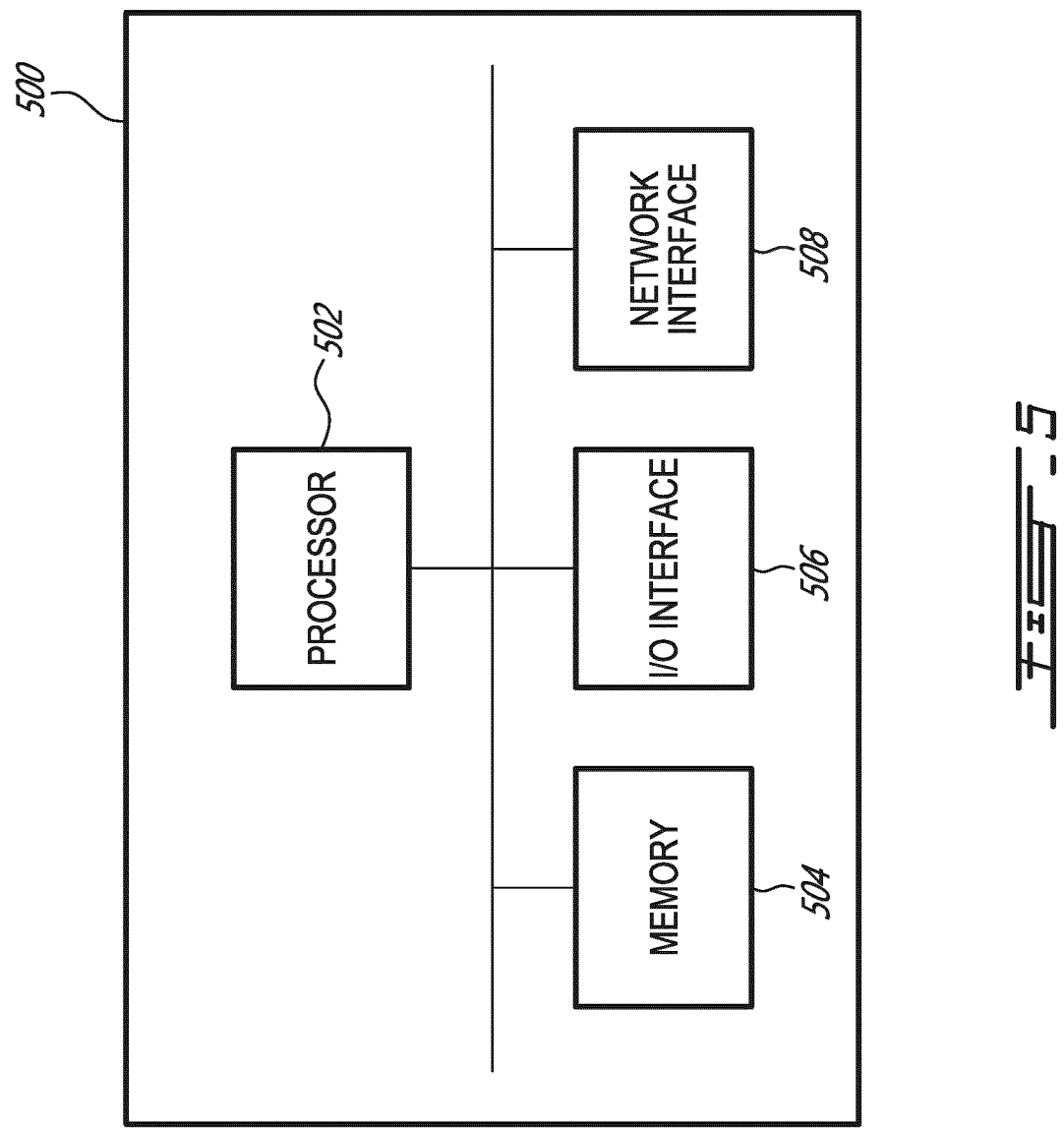

SYSTEMS AND METHODS OF PROVIDING NETWORKS BASED ON TEXTILES

FIELD

The present application generally relates to textile computing systems, and in particular to systems and methods of providing networks based on textiles.

BACKGROUND

A platform of things may include a collection of devices, such as sensors, computing devices, control systems, or the like, for monitoring users, conducting analytics, or for providing notification output to users. The respective devices of the platform may be discrete or standalone devices placed within a user environment.

SUMMARY

Embodiments described herein are directed to a system of smart textiles including one or more sensors for detecting physiological data of a user and one or more actuators for providing feedback to a user or adapt an environment to the user's requirements. In some examples, the system may be configured to determine user wellness or user identity and, in response, to provide feedback to the user or to adapt the environment to the user. In some examples, the system may determine user identity based on detecting biometric data.

In one aspect, the present application may provide a workspace system. The workspace system may include an electrical interconnection bus, a plurality of disparate textiles respectively coupled to the electrical interconnection bus, and a computing device coupled to the electrical interconnection bus to receive sensor data from at least one of the plurality of disparate textiles. The respective disparate textiles may have incorporated thereon a textile structure providing at least one of a sensor or an actuator. The disparate textiles may be respectively associated with a workspace surface.

In some embodiments, the workspace surface may include at least one of a floor textile, a tabletop textile, a space division textile, or a seating textile.

In some embodiments, the workspace surface may include a non-garment textile.

In some embodiments, the textile structure may include at least one of an electrical, mechanical, or electro-mechanical structure.

In some embodiments, the respective plurality of disparate textiles may include at least one of shape shifting alloy yarn, thermal yarn, piezoelectric yarn, electromagnetic yarn, or electrical stimulation fiber.

In some embodiments, the respective disparate textiles may include one or more fibers configured as the sensor to detect a physiological parameter of a user interacting with a respective disparate textile.

In some embodiments, the electrical interconnection bus may include a bi-directional interconnection bus configured to conduct at least one of a power or data signal to at least one of the plurality of disparate textiles.

In some embodiments, the electrical interconnection bus may include an inductive charging circuit to provide power to at least one of the plurality of disparate textiles.

In some embodiments, the workspace system may include a power transformer configured to transform power signals for at least one of the plurality of disparate textiles.

In some embodiments, the electrical interconnection bus may include at least one of a wired or wireless interconnection bus.

In some embodiments, the respective plurality of disparate textiles may include one or more fibres configured as the actuator to provide feedback to a user based on the received sensor data from the at least one of the plurality of disparate textiles.

In another aspect, a non-transitory computer-readable medium or media having stored thereon machine interpretable instructions which, when executed by a processor may cause the processor to perform methods described herein.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the present disclosure.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 3 illustrates a schematic diagram of a disparate textile, in accordance with an embodiment of the present application;

FIG. 4 illustrates a workspace system including a plurality of disparate textiles integrated to a plurality of respective fixtures or objects, in accordance with an embodiment of the present application; and FIG. 5 illustrates a block diagram of a computing device, in accordance with an embodiment of the present application.

DETAILED DESCRIPTION

Systems and methods described herein include disparate textiles integrated with fixtures or objects. The respective disparate textiles may be interconnected via electrical interconnection busses and may include electrical, mechanical, and/or electro-mechanical structures for sensing physiological data of users and for providing, based on the sensed physiological data, actuator output to one or more disparate textiles for personalizing a workspace.

In some embodiments, the respective disparate textiles may be included on surfaces that a user may customarily contact or interact with in a course of occupying a workspace. Thus, embodiment systems and methods described herein may provide a textile computing network for monitoring a workspace environment or for monitoring a physiological state of one or more workspace users and, in response to detected workspace or user data, adaptively personalize a workspace for the one or more workspace users.

The term "connected" or "coupled to" may include both direct coupling (in which two elements that are coupled to each other contact each other) and indirect coupling (in which at least one additional element is located between the two elements).

Figure 1:
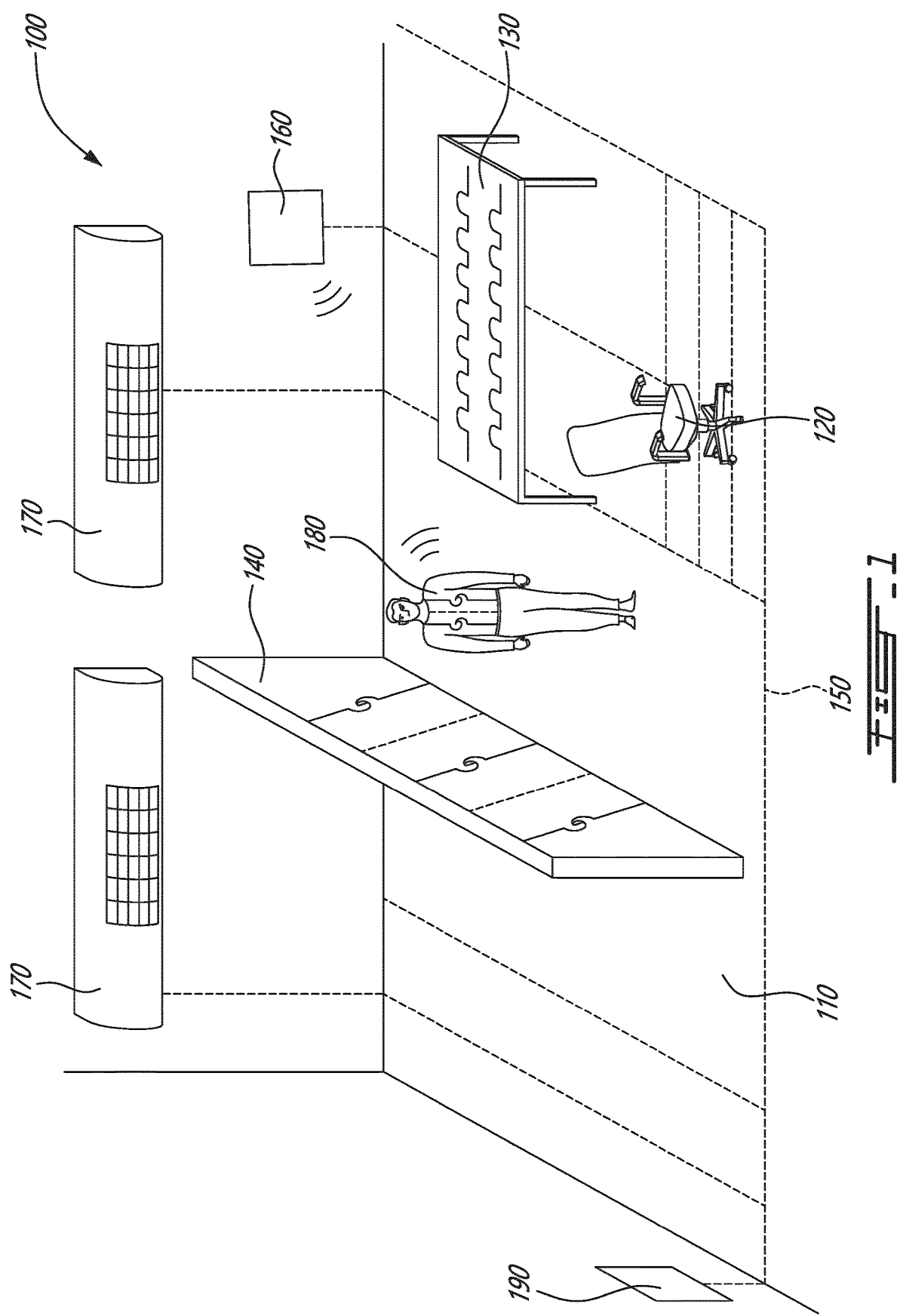
FIG. 1 illustrates a workspace system, in accordance with an embodiment of the present application.

Reference is made to FIG. 1, which illustrates a workspace system 100, in accordance with an embodiment of the present application. The workspace system 100 can include a plurality of disparate textiles in a workspace. The respective disparate textiles may be a component of or integrated with an associated fixture or object of the workspace. The workspace may be an office workspace, a classroom workspace, a home workspace, or the like, containing fixtures or objects. In some embodiments, the fixtures or objects may include flooring, seating furniture, tables, room division panels, or the like. The fixtures may include the disparate textiles interwoven or integrated therein.

In FIG. 1, the workspace system 100 includes flooring textile 110, seating textile 120, tabletop textile 130, and space division textile 140. Other textiles integrated within fixtures may be contemplated. The respective fixtures or objects may include a textile component integrated therein such that a user may touch or interact with the textile component. In some examples, a textile may be a flexible material consisting a network of natural or synthetic fibers, such as animal-based material (e.g., wool or silk), plant-based material (e.g., linen or cotton), or synthetic material (e.g., polyester or rayon). Other types of textiles may be contemplated.

In some embodiments, the respective disparate textiles may have incorporated therein a textile structure for providing an electrical, mechanical, or electro-mechanical structure. The textile structure may include electrical conductive circuits, sensors, actuators, or other types of data acquisition or feedback components. In some examples, electrical, mechanical, or electro-mechanical fibers, such as piezoelectric, electromagnetic, shape shifting, etc. yarns, may be warp knitted into a textile along the length of the textile fabric. For instance, electro-mechanical fibers may be weaved in a "zig-zap" pattern across textile fabric to provide sensor or actuator structures for the disparate textiles. Conductive paths or textile structures may be integrated into textiles by one or a combination of methods including inlaying, knitting, weaving, adhesive bonding, or mechanical bonding. Other methods of integrating conductive paths into textile structures may be contemplated.

In examples where haptic feedback may be provided, the respective disparate textiles may include a combination of discrete piezoelectric vibrators (or similar device for providing haptic feedback) and electro-mechanical fibers integrated into a disparate textile for providing haptic feedback to a user.

In some examples, the respective textiles may be configured to include sensing structures, such as pressure sensing structures, biometric sensing structures, physiological sensing structures, or the like for receiving touch controls, for detecting user occupancy or user positioning, for detecting physiological data from a user, or other types of data. In some examples, physiological data may include electrophysiological metrics such as heart rate variability, hydration metrics, respiration metrics, or the like for detecting a user physiological state (e.g., fatigue, stress, anxiety, etc.). In some examples, physiological data may include sensed data relating to biomechanics, hemodynamics, biochemical, or electrophysiology. Other types of sensed data corresponding to physiological metrics may be contemplated.

In some examples, the respective textiles may be configured to include power or data transmission structures for wired or wireless data or power transmission. As will be described herein, the respective textiles may be coupled to an electrical interconnection bus. The electrical interconnection bus may be configured as a bi-directional bus for transmitting or receiving signals, such as data signals, power signals, or other type of signals that may carried on the electrical interconnection bus. In some examples, the power transmission structures may be an inductive charging circuit for charging electrical devices positioned near or adjacent to the power transmission structure of the respective textile.

In some examples, the respective textiles may be configured to include actuating structures for temperature control, lighting control, haptic output, air flow control, noise control, or other types of control. For example, in response to supply of electrical current, the respective textiles may include conductive yarns configured to distribute or dissipate heat. In some examples, the respective textiles may include structures having electroluminescence properties or light-emitting diodes for providing lighting. Other types of textiles configured to provide actuating structures may be contemplated.

Textiles may include one or more types of fibers. In some embodiments, the textiles may include shape shifting yarn. For example, the shape shifting yarn may be shape shifting alloy yarn that may contract or expand when thermally or electrically heated. The shape shifting yarn may be configured to provide one or more sensors for detecting interaction with a user or may be configured to provide one or more actuators to a user.

In some embodiments, the textiles may include thermal yarn fibers, which may be yarns having resistive and/or electrostatic properties configured to generate/conduct heat based on application of electrical current thereto. In some examples, the textile may be configured to include thermal yarn fibers having a range of resistive properties for configuring a desirable sensor or actuator.

In some embodiments, the textiles may include piezoelectric yarns having shape shifting, heating, or other properties for configuring piezoelectric yarns as a sensor.

In some embodiments, shape shifting or shape memory materials include materials that change shape from a defined shape to a deformed shape in response to external stimulus. In some examples, shape shifting materials may change shape in response to changes in environment temperature, physical stress, magnetic field, electric field, presence of UV light, or moisture.

Shape shifting or shape memory materials may include metallic shape memory alloys, such as nickel-titanium alloys (NiTi), and copper-based alloys, such as CuZnAl and CuAlNi. Shape memory alloys have properties allowing the material to recover from physical strain or to generate physical force when changing shape.

Metallic shape memory alloys may be knitted as fibers or wire traces into textile fabrics. In some embodiments, when metallic shape memory alloys are wrapped, drawn, knit, or weaved into textile fabrics, the metallic shape memory alloys may be in an austenite phase. In some examples, the shape memory alloys may be coupled with polyparaphenylene terephthalamide (PPTA), high tenacity polyethylene (PE) and aramid yarns.

In some embodiments, shape shifting or shape memory materials may include shape memory polymers. A combination of shape memory polymers may be integrated with textile fabrics and may be responsive to external stimulus, such as heat, moisture, electric field, magnetic field, or the presence of UV light. In some examples, shape memory polymers responsive to heat may transition from a deformed temporary shape to a defined shape in response to heat above a threshold activation temperature. The defined shape may be associated with polymer cross-links, whereas the deformed temporary shape may be associated with triggering segment structures having a thermal transition temperature range. In some examples, shape memory polymers may be thermoplastic elastomers or thermosets.

In some embodiments, shape memory polymers may be integrated into textile fabrics as fibers, coatings or membranes, or knit or woven structures. Textiles including shape memory polymers may change shape based on Micro-Brownian motion or thermal vibration of polymer particles when an environment temperature increases above a predetermined threshold temperature. The polymer particles may cause micro pores, or free spaces, to form within the textile fabric, thereby allowing water vapour or gaseous substances to permeate the textile fabric. In some examples, water vapour permeating the textile fabric may be absorbed before being able to condense. The absorbed vapour may be conducted into or diffused through the textile fabric and passed through to an opposing side of the textile fabric. The present example describes shape memory polymers that may alter shape in response to temperature changes; however, other examples may include shape memory polymers that may alter shape in response to other external stimulus, such as electric field, magnetic field, or the like.

Table 1 provides examples of shape memory polymers that may be integrated with embodiments of disparate textiles described herein, and physical properties of the shape memory polymers, in accordance with embodiments of the present disclosure.

TABLE 1

Shape memory polymer and mechanisms

| | Physical Interactions | |
| --- | --- | --- |
| Polymers | Original Shape | Transient Shape |
| Polynorbornene | Chain entanglement | Glassy state |
| Polyurethane | Microcrystal | Glassy state |
| Polyethylene/nylon 6 graft copolymer | Crosslinking | Microcrystal |
| Styrene-1,4-butadiene block copolymer | Microcrystal/Glassy state of polystyrene | Microcrystal of poly(1,4-butadiene) |
| Ethylene oxide-ethylene terephthalate block copolymer | Microcrystal of PET | Microcrystal of PEO |
| Poly(methylene-1,3-cyclopntane) polyethylene block copolymer | Microcrystal of PE | Glassy state/micro crystal of PMCP |

In some embodiments, the textiles may include electromagnetic yarns having, for example, ferromagnetic properties suitable for providing haptic feedback to a user.

In some embodiments, the textiles may include electrical stimulation fibers having, for example, properties for transmitting electrical pulses to a skin of a user for providing tactile sensation to a user.

In some embodiments, fibers with electrical, mechanical, or electro-mechanical properties may be conductive fibers or non-conductive fibers. In some examples, metallic yarn or fibers may be knitted with non-conductive fibers and the metallic yarn may be configured to provide electrically conductive traces across a surface of the textile.

The fibers may be include copper fibers, brass fibers, or the like. Because example disparate textiles described herein may be configured to interact with or interface with a user, in some examples, metallic fibers that may cause allergic reactions in users (e.g., nickel fibers as an example) may not be used for constructing the plurality of disparate textiles.

Other types of fibers having other example electrical, mechanical, or electro-mechanical properties configured to provide sensory or haptic feedback features may be contemplated.

The flooring textile 110, chair textile 120, tabletop textile 130, and space division textile 140 of FIG. 1 may respectively be coupled to an electrical interconnection bus 150 for providing the workspace system 100 of FIG. 1. The electrical interconnection bus 150 may include a network of fibers or yarns for conducting power signals or data signals to the plurality of disparate textiles coupled thereto. The network of fibers or yarns may have electrical conductive properties and may be configured to provide interconnection of one or more disparate textiles of the workspace system 100. In some embodiments, the electrical interconnection bus 150 may be configured as a bi-directional bus for carrying signals, such as power signals, data signals, or other types of signals that may be transmitted on the bus.

In some examples, the fibers or yarns may include anti-abrade or anti-cut properties for withstanding physical contact with users, hydrophobic properties for preventing electrical shorts or faults, or other properties for protecting the electrical interconnection bus 150 from electrical faults or mechanical faults.

As illustrating examples, the seating textile 120 may be integrated with an office/task/computer chair, a bench, or other type of seating fixture. The tabletop textile 130 may be integrated with a desk surface, such as a computer desk, an office desk, or other type of work surface that a user may interact with. The space division textile 140 may be integrated with building walls, cubicle panels, room division panels, or the like.

In FIG. 1, the electrical interconnection bus 150 is illustrated as a plurality of hatched lines routed in a grid-like pattern. In some embodiments, other routing layouts of the electrical interconnection fibers or threads may be contemplated. For example, the electrical interconnection fibers or threads may have a greater density in areas corresponding to greater user traffic or greater density of furniture or fixtures. In some embodiments, the electrical interconnection bus 150 may also include electrical interconnection fibers or threads of the respective textiles. For example, in FIG. 1, the electrical interconnection bus 150 may include some of the fibers or threads of the flooring textile 110. The electrical interconnection bus 150 may include any number of or varied physical layout of electrical interconnection fibers or threads for coupling the respective disparate textiles or computing devices of the workspace system 100 to other textiles or computing devices of the workspace system 100.

In some embodiments, the workspace system 100 includes a computing device 160 coupled to the electrical interconnection bus 150. The computing device 160 includes a processor, a memory coupled to the processor, and a communication circuit coupled to the processor. As will be described herein, the memory may include processor readable instructions that, when executed by the processor, may configure the processor to receive sensor data from at least one of the plurality of disparate textiles or to transmit actuator instructions to the at least one of the plurality of disparate textiles.

In some embodiments, the processor readable instructions may transmit actuator instructions to actuators integrated within textiles of the workspace system 100 for adapting or modifying the workspace environment conditions to defined user requirements. For example, the processor readable instructions may transmit power and/or data signals via the electrical interconnection bus to one or more disparate textiles for providing feedback to a user or for providing a discernable output to a user of the workspace system 100.

For example, the electrical interconnection bus 150 or the one or more disparate textiles may include a network of resistive electrically conductive fibers and, in response to identifying that an environment temperature is below a defined threshold, the processor readable instructions may include power signals causing a portion of the network of resistive electrically conductive fibers to generate heat.

In another example, the processor readable instructions may configure the processor to receive from a seating textile 120 pressure sensor data from an office chair, determine whether a user of the office chair is seated in an ergonomically sound seating position based on the pressure sensor data, and, in response to determining that the user is not seated in an ergonomically sound seating position, transmit data signals for activating one or more actuating structures of the seating textile 120 for providing haptic feedback at one or more portions of the seating textile 120. The haptic feedback may guide the user into an ergonomically sound seating position.

In another example, the workspace system 100 may include one or more heating, ventilation, and air conditioning (HVAC) units 170 electrically coupled to the electrical interconnection bus 150. The workspace system 100 may be configured to receive sensor data from one or more disparate textiles, such as the flooring textile 110, chair textile 120, the tabletop textile 130, or the space division textile 140. The workspace system 100 may be configured to determine current workspace environment conditions based on one or a combination of the received sensor data and to generate actuator instructions to facilitate adjustment or to adjust environment conditions of the workspace. The computing device 160 of the workspace system 100 may transmit actuator instructions to actuators integrated within the HVAC units 170 for adjusting environment conditions of the workspace. In a scenario where sensor data from the flooring textile 110 or the space division textile 140 indicate that the workspace temperature is less than a threshold value, the actuator instructions may configure the HVAC units 170 to force warmed air into the workspace. By combining environment sensor data from a plurality of disparate textile surfaces, the workspace system 100 may facilitate adjustment of workspace environment conditions based on a combination of sensor data from a plurality of disparate textiles.

In some embodiments, the processor readable instructions for determining whether to transmit signals to one or more disparate textiles for providing feedback by the disparate textile may be conducted at a remote device and the result of the determination may be transmitted to the computing device 160. In some other embodiments, processor readable instructions for determining whether to or when to provide feedback output at a disparate textile may be conducted at a computing device associated with the respective disparate textiles. Other example use cases of the workspace system 100 will be described herein.

In some embodiments, the workspace system 100 may include a garment textile 180, such as a clothing garment configured to be worn by a user. For example, the garment textile 180 may include a shirt having electrically conductive fibers interwoven therein for detecting physiological data from a wearer of the garment textile 180 and for providing haptic feedback (e.g., vibratory feedback, heat feedback, etc.) to the wearer of the garment textile 180. In some embodiments, the garment textile 180 may be configured to interface with a computing module for detecting said physiological data of the wearer or for providing data signals for triggering haptic feedback to the wearer of the garment textile 180. In some embodiments, the computing module may detect physiological data of the wearer, such as electrocardiogram (ECG) signals, and may deduce an identity of the wearer of the garment textile 180. In some examples, the computing module may deduce user identity based on detected heart rate variability data. The garment textile 180 may be configured as a user identification interface device, where user identification may be based on detected physiological data of the wearer. In some embodiments, the computing module may conduct operations to customize haptic feedback provided to the wearer of the garment textile 180 based on the deduced identity of the wearer. As will be described herein, in some examples, the computing module may deduce the identity of the wearer of the garment textile 180 for use in combination with data from other user detecting sensors for enabling or adapting a workspace for the identified user.

In some embodiments, the computing device 160 may include a wireless communication circuit for receiving or transmitting wireless data signals from or to one or more disparate textiles. For example, the computing device 160 may transmit or receive wireless data signals to or from a wireless communication circuit of the garment textile 180. Other disparate textiles of the workspace system 100 may include wireless communication circuits for wirelessly transmitting or receiving data signals to or from the computing device 160 or any other device coupled to the electrical interconnection bus 150.

In some embodiments, the electrical interconnection bus 150 may be configured to provide a mesh data network or mesh power network among the plurality of disparate textiles. For instance, a first disparate textile may be configured to transmit or receive data signals to or from a second disparate textile via the configured mesh network.

In some embodiments, the electrical interconnection bus 150 may be coupled to a mains electricity 190 for distributing power to the disparate textiles and/or the computing devices of the workspace system 100. For example, the mains electricity 190 may be a general-purpose alternating-current (AC) electric power supply for delivering power to the workspace system 100. In some examples, the mains electricity 190 may be configured to provide 120V at an AC frequency of 60 Hz. In some other examples, the mains electricity 190 may be configured to provide 230V at an AC frequency of 50 Hz. Other combinations of voltage and AC current frequency may be contemplated.

In some embodiments, the electrical interconnection bus 150 may include one or more alternating-current to direct-current (AC/DC) converters (not illustrated in FIG. 1) for stepping down or modifying the electrical output of the mains electricity 190 to a voltage/frequency corresponding to an electrical rating of the respective disparate textiles. In some embodiments, the electrical interconnection bus 150 may include one or more direct-current to direct-current (DC/DC) converters for stepping up or stepping down voltage levels for consumption by one or more disparate textiles.

Figure 2:
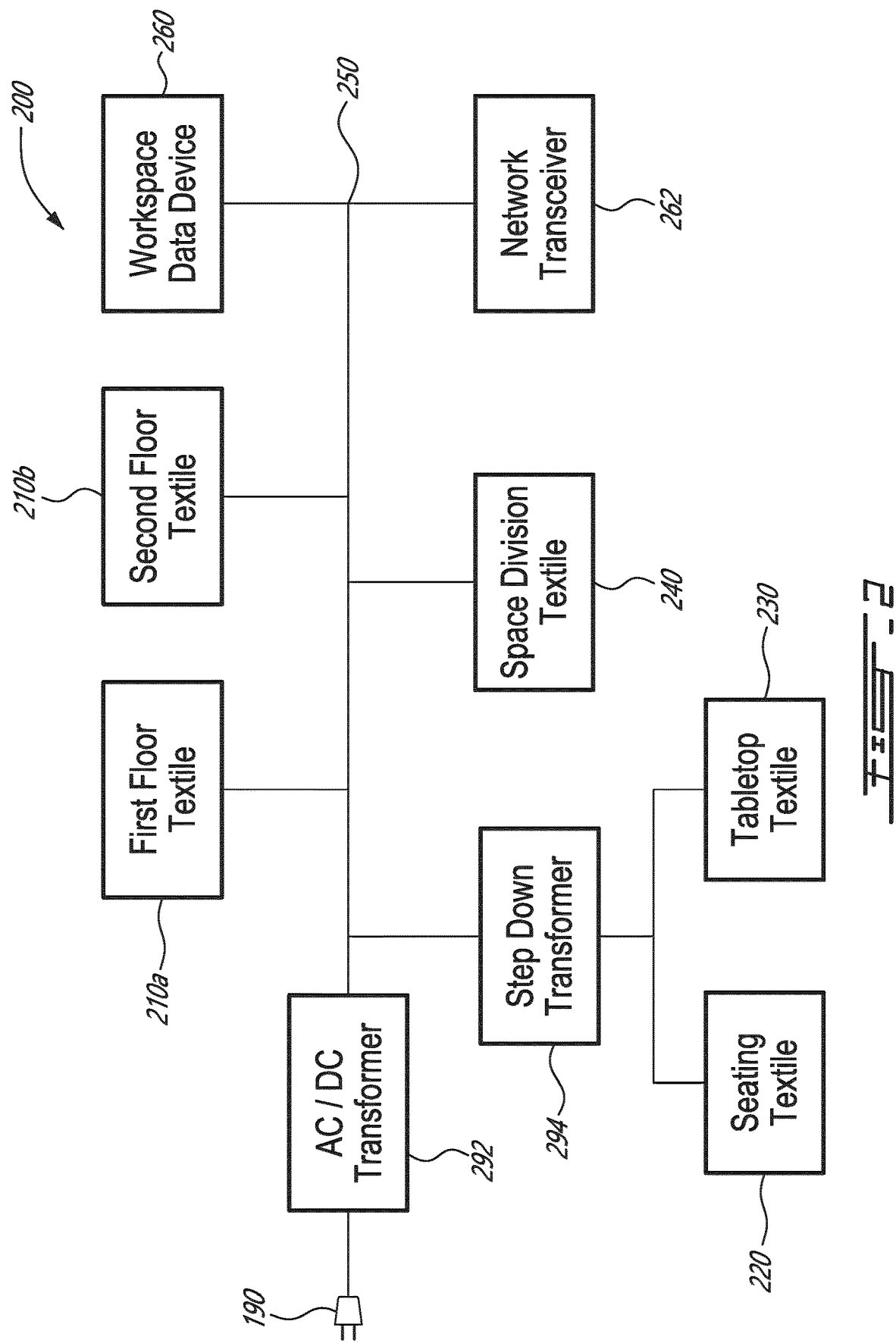
FIG. 2 illustrates a schematic diagram of a workspace system, in accordance with an embodiment of the present application.

Reference is made to FIG. 2, which illustrates a block diagram 200 of a workspace system, in accordance with an embodiment of the present application. The block diagram 200 may correspond to the example workspace system 100 of FIG. 1.

The workspace system may include an electrical interconnection bus 250. In some embodiments, the electrical interconnection bus 250 may provide a textile power network for a plurality of disparate textiles. The electrical interconnection bus 250 may be coupled to a mains electricity 290 for providing power to the plurality of coupled disparate textiles. The electrical interconnection bus 250 may include a combination of one or more electrically conductive threads or fibers of one or more disparate textiles. The respective disparate textiles may be electrically coupled to the electrical interconnection bus 250.

As illustrated in FIG. 2, each of a first floor textile region 210a, a second floor textile region 210b, a seating textile 220, a tabletop textile 230, or a space division textile 240 may be coupled to the electrical interconnection bus 250 for receiving power. It may be appreciated that other types of disparate textiles for any other fixtures may be coupled to the electrical interconnection bus 250. For example, one or more disparate textiles may be integrated into a door, a window covering (e.g., curtain), a room divider (e.g., wall, partition, etc.), or a ceiling of a building or room. Other types of fixtures having disparate textiles integrated thereon are contemplated. In some embodiments, a workspace data device 260 and a network transceiver 262 may be coupled to the electrical interconnection bus 250.

In some examples, the network transceiver 262 may be a local wireless data hub or data router for receiving or transmitting data from/to textiles (e.g., garment textiles) or other computing devices. To illustrate, the network transceiver 262 may be configured to wirelessly receive sensor data from a garment textile (not illustrated in FIG. 2) worn by a user and to transmit, via the electrical interconnection bus 250, the received sensor data to the workspace data device 260. In some examples, at least a portion of the electrical interconnection bus 250 may be configured as a wireless data connection.

In some examples, a mains electricity 290 may be coupled to the electrical interconnection bus 250 may provide electricity having 230V/50 Hz (or any other voltage/frequency combination). The workspace system may include an AC/DC transformer 292 for transforming output of the mains electricity 290 to a corresponding operating voltage/frequency of one or more disparate textiles. For example, the first floor textile region 210a or the space division textile 240 may include electrical, mechanical, or electrical-mechanical structures operating at a voltage/frequency different than that provided at the output of the mains electricity 290.

In some embodiments, the workspace system may include a DC/DC step down voltage converter 294 for transforming an output of the AC/DC transformer 292 to a voltage level corresponding to a corresponding operating voltage of one or more disparate textiles. For example, the seating textile 220 associated with an office chair or the tabletop textile 230 associated with a desk or table may include electrical, mechanical, or electrical-mechanical structures operating at a voltage level different than that provided by the AC/DC transformer 292.

In some embodiments, the first floor textile 210a and/or the second floor textile 210b may include electrically conductive fibers for providing at least a portion of the electrical interconnection bus 250 and one or more other disparate textiles may be coupled to one or more electrically conductive fibers of the floor textile for transmitting or receiving power signals. That is, one or more disparate textiles may be configured to provide power signals to adjacent disparate textiles. The textile power network illustrated in FIG. 2 is exemplary and other textile power network topologies or configurations may be contemplated.

In some embodiments, the electrical interconnection bus 250 may provide a textile data network for a plurality of the disparate textiles. The respective disparate textiles may transmit/receive data to/from one or more other disparate textiles via the electrical interconnection bus 250. In some embodiments, the workspace system may include the workspace data device 260 for retrieving sensor data signals from one or more disparate textiles and for transmitting actuating data signals for configuring one or more disparate textiles to provide feedback to a user. Based on the actuating data signals, the one or more disparate textiles may provide feedback via one or more electrical or mechanical structures (e.g., luminescence feedback, vibratory feedback, heat feedback, etc.). Thus, the workspace data device 260 in combination with the electrical interconnection bus 250 may be configured to aggregate data signals received from one or more disparate textiles and provide one or more feedback data signals to a disparate textile based on one or a combination of the aggregated data signals.

To illustrate an application of the workspace system as a textile data network, a user may be wearing a garment textile (not illustrated in FIG. 2) that may be wirelessly coupled to the workspace data device 260 via the network transceiver 262 and the electrical interconnection bus 250. When the user may be seated at a desk surface having the tabletop textile 230 incorporated therein, workspace data device 260 may receive physiological or bio-signal data from both the garment textile and the tabletop textile 230 (e.g., when the user is seated at the desk surface with wrists placed adjacent a portion of the tabletop textile 230 for typing at a keyboard) and determine whether a physiological data signal (e.g., electrocardiogram data signal) received from a garment textile worn by a user substantially matches another physiological data signal received from a tabletop textile 230. In the scenario where the workspace data device 260 identifies that the physiological data signals substantially match, the workspace data device 260 may transmit an authentication indication signal for unlocking a computing workstation for the user that is seated at the desk. In some examples, physiological data signals may substantially match if at least a portion of the physiological data signals correspond to a determined criteria. In the present example, the workspace system may be configured to deduce user identity based on a combination of received textile data signals for conducting an action (e.g., unlocking a computing device, adjusting environment temperature to user desired temperature, etc.).

Other example embodiment implementations of the workspace system may be contemplated.

Reference is made to FIG. 3, which illustrates a schematic diagram of a disparate textile 300, in accordance with an embodiment of the present application. The disparate textile 300 may include a network of fibers and one or more sensors 310 or actuators 312. In some embodiments, the one or more sensors or actuators may be integrated or affixed to the disparate textile 300 and interconnected by the network of fibers 320.

In some embodiments, the network of fibers may be configured to provide textile structures, such as electrical components, mechanical components, or electro-mechanical components. For example, one or more fibers of the disparate textile 300 may include shape shifting properties, electrical resistive properties, piezoelectric properties, or other properties suitable for providing the sensors 310 or the actuators 312. The one or more sensors 310 or actuators 312 may be textile structures composed of textile fibres, such as piezoelectric yarn or shape shifting alloy yarn configured to provide sensor signal data or to receive signals for providing actuation output.

The disparate textile 300 illustrated in FIG. 3 may be configured as one of a floor textile, a tabletop textile, a space division textile, or other type of textile. As an illustrating example, the disparate textile 300 of FIG. 3 may be a tabletop textile having a relatively high density of the sensors 310 or actuators 312 on a portion of a desk intended for supporting a computer keyboard or pointing device. The subset portion of the tabletop textile may be configured with a higher density of textile fibers for detecting sensory data or for providing haptic feedback proximal to an area where a user may be most likely to interface with the tabletop textile. Continuing with the present example, while the user may be typing on a keyboard placed atop the tabletop textile, the user's wrists or portions of the user's arm may contact the tabletop textile such that the sensors 310 detect physiological data to detect user heartrate, user respiration, user fatigue/stress/anxiety data points, user presence (e.g., via pressure sensors), or the like.

In some embodiments, one or more fibers may have piezoelectric properties and may be configured such that the structure of the one or more fibers may be used to detect pressure or contact with the tabletop textile for sensing physiological data of the user. In another example, one or more fibers may be shape shifting alloy yarn and may be configured to produce movement or sensory output in response to receipt of electrical signals or current for providing feedback to a user.

In FIG. 3, the network of fibers 320 and the sensors 310 or actuators 312 (either as standalone devices integrated on the disparate textile or as fiber structures) may be provided using a fiber layout routing patterns, such as grid-like patterns, patterns having disparate density portions, or any other layout pattern.

In some embodiments, the network of fibers 320 may be thermally conductive yarns for distributing or dissipating heat. In some embodiments, the network of fibers 320 may be resistive fibers and, when a power signal is transmitted to the resistive fibers, may generate heat. In some embodiments, fibers may be configured as electro-mechanical structure for sensing temperature or other environmental conditions.

In some embodiments, the network of fibers 320 may be configured as electro-mechanical structures for sensing pressure and the disparate textile 300 may include a plurality of integrated pressure sensing structures. In an example of the disparate textile 300 being a floor textile for a workspace environment, the disparate textile 300 may include a plurality of pressure sensing structures for sensing user occupancy or frequency of occupancy within zones of a workspace. For example, a combination of pressure sensing structures positioned throughout the floor textile may be configured to detect user stride length, step length, cadence, speed, dynamic base, progression line, foot angle or pronation, or other characteristics useful for detecting gait of a user. In some examples, the workspace system may deduce a user identity based on gait detection of a user walking across the floor textile.

In some embodiments, the combination of pressure sensing structures positioned throughout floor textiles of a building may be configured to provide sensory data to the workspace system and the workspace system may be configured to determine user occupancy or traffic patterns throughout a building based on a combination of the sensory data collected over time. For example, the workspace system may be configured to determine which rooms within a building may be occupied, the average duration of time that the respective rooms may be occupied for, how frequently the respective rooms may be occupied through the course of a day, week, month, or other types of occupancy tracking measures. In some examples, the workspace system may be configured to generate reports for identifying health and safety concerns, such as overcrowding of subset portions of the building.

In an example of the disparate textile 300 being a tabletop textile, the disparate textile 300 may include pressure sensors configured to function as control buttons and to receive input from a user (e.g., control buttons for height-adjustable tables).

In an example of the disparate textile 300 being a seating textile, the disparate textile 300 may include a combination of pressure sensing structures for determining a user's seating posture in a chair based on pressure data from a plurality of chair regions having the plurality of pressure sensing structures.

In some embodiments, the network of fibers 320 may include electrical structures for providing visible electromagnetic radiation (e.g., electroluminescence properties). For example, the network of fibers 320 may be configured to provide structures akin to light-emitting diodes (LEDs) embedded in floor textiles, space division textiles, or tabletop textiles for illuminating an environment. In some examples, such network of fibers 320 may provide visual cues for identifying vacant/occupied seating structures, desks, rooms, etc. of the workspace. In some examples, the workspace system may be configured to optimize meeting room usage by providing visual cues associated with meeting rooms that may be occupied less often such that the overall frequency of meeting room usage throughout a building may be evenly distributed.

In some examples, such network of fibers 320 may provide dynamic illumination of a workspace in response to sensor data signals received from one or more sensors corresponding to a user's physiological state (e.g., mood, etc.) or corresponding to a time of day. For instance, in response to detecting that a user is physiologically fatigued, the network of fibers 320 may be configured to provide illumination for improving the user's alertness. In some examples, such network of fibers 320 may be configured to provide interactive displays or messaging communication for users of the disparate textile 300. As described in some examples of the present disclosure, the workspace system may be configured to monitor and alter occupancy of a workspace, environment conditions of the workspace, or personal wellness of users of the workspace.

In some embodiments, the network of fibers 320 may include electro-mechanical structures for providing haptic actuators providing feedback for seating textile or workspace textiles. For example, the network of fibers 320 may include shape shifting alloy yarn or electrical stimulation fibers that can provide haptic feedback movement or tactile sensation as a user contacts the network of fibers 320. In some embodiments of a seating textile, haptic feedback may be configured to provide feedback on whether an optimal seating posture or position is detected.

In some embodiments, the disparate textile 300 may be coupled to a power controller 390, such as an AC/DC transformer or a DC/DC converter, such that the disparate textile 300 may receive power at a voltage and/or current frequency rating suitable for operation of the respective sensors 310, actuators 312, and/or network of fibers 320.

In some embodiments, the disparate textile 300 may include a plurality of fibers configured to provide inductive charging circuits, such that when a first disparate textile may be positioned adjacent or in close proximity to a second disparate textile, the first disparate textile may include electro-mechanical structures for providing inductive charging functionality to a device corresponding to the second disparate textile. The charging circuits may be knit, embroidered, sewn, laminated, or imprinted to a disparate textile for creating an inductive charging circuit. Other modalities of integrating charging circuits on a disparate textile may be contemplated. When charging circuits are integrated onto disparate textiles, charging circuits may be provided on tabletop surfaces, flooring surfaces, space division surfaces (e.g., cubicle walls), or seating surfaces, thereby reducing discrete electrical wiring in the workspace. In some examples, magnetic field associated with inductive charging may be substantially normal or perpendicular to the disparate textile surface for inductively charging an electronic device.

In some embodiments, the disparate textile 300 may be coupled to a transceiver 362 for receiving or transmitting data from/to other disparate textiles or other computing devices via an electrical interconnection bus (not explicitly illustrated in FIG. 3).

The physical layout of the network of fibers 320 and/or the layout of the sensors 310 or actuators 312 for the disparate textile 300 that is illustrated in FIG. 3 is exemplary and other physical layouts may be contemplated. Other physical layouts may be based on whether the disparate textile may be a floor textile, a tabletop textile, a space division textile, and/or a seating textile. In some examples, the physical layout of the disparate textile may be based on a target functional configuration of the disparate textile 300.

To illustrate applications of a workspace system having one or more disparate textiles coupled to an electrical interconnection bus for providing at least one of a textile data network or a textile power network, reference is made to FIG. 4, which illustrates a workspace system 400 including a plurality of disparate textiles integrated to a plurality of respective fixtures or objects, in accordance with an embodiment of the present application.

The workspace system 400 may include a plurality of disparate textiles including: a floor textile 410, such as a smart carpet or textile floor mat, integrated into a workspace floor; a seating textile 420, such as smart chair paneling, integrated into an office chair; and a tabletop textile 430, such as a tabletop surface, integrated into an office desk. The plurality of disparate textiles may include space division textiles 440 integrated into room dividers, walls, or the like.

The plurality of disparate textiles may be respectively coupled to an electrical interconnection bus. In some embodiments, the electrical interconnection bus may include portions of fibers from one or more of the disparate textiles interconnecting the respective disparate textiles of the workspace system 400. Textile fibers of the respective disparate textiles and textile fibers configured to form the electrical interconnection bus may include one or a combination of shape shifting alloy yarn, thermal yarn, piezoelectric yarn, electromagnetic yarn, or electrical stimulation yarn. Other types of textile fibers for forming textile structures configured to sense, actuate, and/or conduct power or data signals may be contemplated.

In some embodiments, the workspace system 400 may be configured to monitor and/or manage occupancy of the workspace. For example, the workspace system 400 may be configured to detect utilization of the workspace based on sensor data from at least one of the floor textile 410, the seating textile 420, or the tabletop textile 430. Utilization data may provide "wear and tear" metrics for shared workspaces or amenities and allow a computing device to generate utilization models for optimizing use of the workspace. For example, occupancy or utilization data may be based on sensory input, such as pressure sensor input or other electro-mechanical sensor input.

In some examples, the workspace may include regions (e.g., offices or cubicles) that are dynamically assigned based on utilization data. The plurality of disparate textiles may provide feedback by way of visual output (e.g., electroluminescence), physical output (e.g., haptic), or other types of feedback. The floor textile 410 may include a plurality of electrically conductive fibers arranged in a grid-like pattern across the surface of the floor textile 410. Other arrangements of the electrically conductive fibers may be contemplated. The floor textile 410 may include a plurality of textile fibers configured to provide pressure sensors for identifying heavily utilized floor space (e.g., numerous occupants walking through specific regions during a course of a day) or under-utilized floor space in the workspace based on pressure data from a plurality of pressure sensors distributed about the floor textile 410. In another example, the seating textile 420 may include a plurality of textile fibers configured to provide pressure sensors for detecting occupancy of an associated office chair.

In some examples, in response to identifying occupancy or lack of occupancy of a workspace based on pressure data from a floor textile 410 and/or a seating textile 420, the workspace system 400 may transmit electroluminescence data or power signals to one or more disparate textiles for providing luminescence output via textile fibers (e.g., textile fibers configured to emit visible electromagnetic energy). In some embodiments, in response to identifying occupancy of a workspace, the workspace system 400 may activate/deactivate lighting systems of the workspace. In some embodiments, in response to identifying occupancy of a workspace based on sensory data received from the plurality of disparate textiles, the workspace may activate/deactivate environment condition systems, such as HVAC systems, of the workspace.

In some embodiments, the workspace system 400 may receive sensory data from the plurality of disparate textiles for indicating that an adjacent workspace (e.g., adjacent meeting room or adjacent workplace cubicle) may be occupied by numerous users, indicating that there may be a high level of acoustic noise. The sensory data from the plurality of disparate textiles may include sensory data from flooring textiles, seating textiles, or tabletop textiles detecting presence of users. In some examples, the sensory data may include temperature data from tabletop surfaces or seating surfaces, indicating presence of people. In response to determining that an adjacent workspace may be occupied, the workspace system 400 may transmit actuator signals to one or more space division textiles 440 for acoustic noise dampening. For example, the space division textiles 440 may include sound absorbing materials, such as acoustic foam or acoustic cones 442. In some embodiments, the sound absorbing materials may include shape shifting materials that may be configured to change shape in response to an actuator signal, such as a power signal having a pulsing current or voltage signal or having various amplitudes for causing changes in geometric shape of shape shifting materials.

When the workspace system 400 deduces, based on received sensory data, that an adjacent workspace may be occupied, the workspace system 400 may transmit actuator signals to the sound absorbing materials to alter the geometric shape of the shape shifting material to increase sound absorbing capacity. For example, the actuator signal may configure the sound absorbing material to be reconfigured to include one or more acoustic cones 442 protruding from the space division textile 440 for dampening acoustic noise from adjacent workspaces. In some examples, the acoustic signal may be a pulse-width modulated signal or an amplitude modulated signal associated with inferred noise level (e.g. decibel level) or inferred occupancy of the adjacent workspace, and the pulse-width or amplitude modulated signal may be associated with a range of acoustic cone shapes or depths. Thus, the workspace system 400 may configure shape-shifting materials integrated within disparate textile surfaces to provide sound absorbing structures in response to sensory data associated with occupancy of adjacent workspaces.

In some examples, the floor textile 410 may be configured with a plurality of pressure sensors for detecting occupant steps about the workspace. In some examples, the floor textile 410 may be configured with a plurality of pressure sensors for retrieving pressure data for conducting gait analysis of particular occupants walking about the floor textile 410.

In some embodiments, the workspace system 400 may be configured to deduce occupant identity based on a combination of physiological sensor data collected from two or more disparate textiles and, in response, login or activate a workstation (e.g., computer device, etc.). For example, the workspace system 400 may include a garment textile including textile fibers for providing electrocardiogram (ECG) sensors to detect user physiological data. In the scenario where the garment textile may be assigned to that user, the detected ECG data may be associated with that user. Further, when the user contacts a seating textile 420 (e.g., when sitting in a chair) or when the user contacts a tabletop textile 430 (e.g., when resting wrist or arms on a tabletop surface), the workspace system 400 may compare ECG data detected via the seating textile 420 or the tabletop textile 430 with ECG data detected via the worn garment for identifying the user. The workspace system 400 may login or activate a computing workstation for the identified user based on physiological data detected by the combination of two or more disparate textiles. Other combinations of disparate textiles and associated physiological data detection for user identification may be contemplated.

In some embodiments, the workspace system 400 may be configured to monitor and/or manage environmental conditions of the workspace. For example, the workspace system 400 may be configured to detect temperature, sound, occupant physiological state, or the like and, in response, alter HVAC, lighting, or security features of the workspace.

For example, any one of the disparate textiles of the workspace system 400 may include one or more textile fibres to provide temperature sensors and may generate temperature data associated with an immediate environment proximal to the disparate textile. In response to determining that an environment temperature may be below a desired threshold value, the workspace system 400 may be configured to transmit data signals or power signals to particular textile fibers having resistive properties for generating heat at a seating textile 410 or a floor textile 410. In some scenarios, it may be desirable to generate heat using textiles with which a user may interact with at least because the generated heat may rise from a lower altitude to a higher altitude, thereby providing increased heat generating efficiency as compared to traditional HVAC heating systems.

In some other examples, in response to determining that the environment temperature may surpass a desired threshold value, the workspace system 400 may be configured to transmit data signals or power signals to control traditional HVAC systems for tempering an environment climate of the workspace.

In some embodiments, the one or more space division textiles 440 may include one or more adaptive curtain structures 444. The adaptive curtain structures 444 may include shape-shifting materials that may be configured to alter shape in response to an external stimulus. In some examples, The adaptive curtain structures 44 may include shape-shifting material configured to provide apertures that may enlarge or shrink. For example, when the workspace system 400 determines, based on received sensory data from a plurality of disparate textiles, that the workspace humidity or temperature may be increasing, the workspace system 400 may transmit one or more actuator signals to the space division textiles 440 for enlarging apertures of adaptive curtain structures 444 to promote airflow. In some examples, the one or more actuator signals may be pulse-width or amplitude modulated signals that may configure shape-shifting materials integrated in the adaptive curtain structures 444 for configuring aperture size. In some embodiments, the adaptive curtain structures 444 may also be configured based on temperature stimulus. The shape-shifting material integrated in the adaptive curtain structures 444 may alter shape to enlarge apertures in response to rising temperature.

In some embodiments, the plurality of disparate textiles may be configured to provide a textile power network for providing power charging capabilities for fixtures or objects associated with textiles of the workspace system 400. For example, the floor textile 410 (e.g., smart carpet) may include textile fibers configured to provide inductive charging structures for charging power storage components of the seating textile 420. In some examples, the floor textile 410 may be configured with fibers having piezoelectric properties, such that power signals may be generated in response to mechanical stresses being applied to the floor textile 410. In some embodiments, the generated power signals may be transmitted to other components of the system for charging external devices or for providing power to components of other disparate textiles of the system.

In some embodiments, one or more disparate textiles may be configured with fibers having photovoltaic properties for generating power signals and transmitting the power signals to other textiles coupled to the interconnection bus. For example, window coverings (e.g., curtains) may include fibers configured to convert solar energy into power, and the interconnection bus may be configured to transmit the generated power signals to other disparate textiles of the system. In some embodiments, the generated power signals may be transmitted to other components of the system for charging external devices or for providing power to components of other disparate textiles of the system.

In some embodiments, the seating textile 420 may include textile fibers configured to provide pressure sensors (e.g., occupancy sensors) and the seating textile 420 may be configured to (1) charge electrical power storage components, via the inductive charging structures of the floor textile 410, when the seating textile 420 pressure sensors indicate that the office chair may be unoccupied; and (2) halt charge of electrical power storage components when the seating textile 420 pressure sensors indicate that the office chair may be occupied. In some examples, electrical power storage components may be charged via the seating textile 420 and electrically conductive structures through a frame or base of the office chair. In some embodiments, the seating textile 420 may include electrical power storage components for powering textile structures, such as sensors or actuators, or for providing a mobile source of power via device connectivity with the office chair. In the present example, power storage components (e.g., batteries) may be configured to store sufficient power to provide power to sensors, actuators, or other electrical components integrated in the office chair for 8 or more hours.

In some embodiments, the seating textile 420 may include electrical contact pads that may interface with electrical contact pads in a floor textile 410, such that the floor textile 410 may transfer power to the seating textile 420.

In some embodiments, the tabletop textile 430 may have textile structures including a first inductive charging structures 432 for charging power storage devices of the seating textile 420 (e.g., smart chair). In some embodiments, the tabletop textile 430 may include a portion positioned at an underside of a work desk. Further, the seating textile 420 may include corresponding second inductive charging structures 422. When the seating textile 420 may be positioned proximal to the tabletop textile 430 (e.g., when a smart chair may be tucked into the work desk), the power storage devices of the seating textile 420 may be charged based on the proximal position of the first inductive charging structures 432 and the second inductive charging structures 422.

In some embodiments, the workspace system 400 may be configured to monitor and/or manage physiological status of an occupant of the workspace and, in response, provide feedback to the occupant configurable for enhancing the user's physiological state.

In some examples, the seating textile 420 may include a plurality of textile fibers configured to provide pressure sensors positioned at multiple locations across the seating textile 420. The seating textile 420 may be configured to generate a pressure sensing map for deducing an occupant's seating position. For example, an office chair may include one or more sensors positioned on a chair backing for detecting a user's shoulder position, a user's back position, or a user's hip position. The office chair may include one or more sensors on a seating surface for detecting leg or thigh position. Based on the sensory data, the workspace system 400 may determine whether the user's seating position may be ergonomically efficient. Further, the seating textile 420 may include a plurality of textile fibers configured to provide haptic feedback. In the present example, the workspace system 400 may be configured to identify the extent that the occupant seating posture or positioning is ergonomically sound and, in response, provide haptic feedback for guiding a user to a more ergonomically sound seating position.

In some examples, the seating textile 420 may include a plurality of textile fibers configured to provide one or more sensors for detecting physiological data of a user. For example, the one or more sensors may include contact or non-contact electrocardiogram (ECG) sensors, galvanic skin response (GSR) sensors, bioelectrical impedance analysis (BIA) sensors, or other sensors for identifying a physiological state, such as stress, hydration, heart rate, respiration pattern, or the like, of an occupant. The seating textile 420 may be configured such that the example bio-sensors 424 for detecting physiological data of the user may be positioned on an armrest of an office chair. The example bio-sensors 424 may detect physiological data of the user during the user's customary usage of the seating textile 420 based on an arm being rested on a chair armrest (e.g., the user may not need to intentionally place a finger against a sensor for the express purpose of physiological data collection).

In the present example, the workspace system 400 may be configured to identify a physiological state representing well-being of the user and, in response, adapt the workspace to enhance the well-being of the user. For instance, the workspace system 400 may, in response to the physiological data, adjust colour temperature output of lighting fixtures within the workspace, initiate heat generation by textile fibers of the seating textile 420, adjust ventilation in the workspace, initiate noise damping devices in the workspace (e.g., trigger white noise generators, initiate noise damping structures, etc.), or initiate other devices for altering environmental conditions for enhancing user well-being. Similarly, other disparate textiles of the workspace system 400 may identify physiological data of a user and, in response, provide feedback to the occupant configurable for enhancing the user's physiological state. The tabletop textile 430 may include a plurality of textile fibers configured to provide one or more sensors for detecting physiological data when a user interacts with the tabletop textile 430. For example, the tabletop textile 430 may be located at tabletop positions where a computer user may rest wrists or arms while typing on a keyboard.

In some embodiments, the workspace system 400 may be configured to receive sensory data from a plurality of disparate textiles and to associate the respective sensory data with identified users within a workspace. In some examples, the workspace system 400 may deduce user identity based on ECG signals detected via a user interface with a disparate textile and the workspace system 400 may generate a deduced attendance list of users attending a meeting in the workspace. In another example, the workspace system 400 may be configured to receive sensory data associated with the plurality of meeting attendees within the work space, and the workspace system 400 may generate physiological status (e.g., respective attendee alertness, fatigue level, etc.) of the respective meeting attendees. In response to the generated physiological status of the meeting attendees, the workspace system 400 may transmit actuator signals to the plurality of disparate textiles within the workspace for altering the environmental conditions of the workspace (e.g., increase lighting levels, increase air flow in the work space, etc.). In some examples, the workspace system 400 may generate and transmit a meeting attendee physiological status report to the meeting organizer, such that the meeting organizer may dynamically determine, in near real-time, whether one or more meeting breaks or whether adjustments to the meeting agenda may be desirable.

In some embodiments, the workspace may be configured to couple to remote workspaces (e.g., in other physical office locations). The workspace system 400 may be configured to receive sensory data from a plurality of disparate textiles in the respective workspace locations. In some examples, the sensory data may include biometric data or identity information via ECG signals of meeting attendees, and the workspace system 400 may be configured to validate the identity of meeting attendees in remote workspace locations. Validating identity of meeting attendees in remote workspace locations may be desirable in scenarios where the meeting includes discussion of confidential or private matters. In some examples, the workspace system 400 may be configured to utilize the sensory data received from the disparate textiles in the respective workspace locations to generate dashboard interfaces, such as display interfaces, for providing seating maps (e.g., based on detected biometric data) at respective workspace locations or for providing augmented or virtual reality display outputs.

Embodiments described herein are described with reference to disparate textiles being included on surfaces that a user may contact or interact with in the course of occupying a workspace. Other types of spaces may be contemplated. For example, embodiments described herein may be configured in connected home/residential spaces, manufacturing spaces, or other environments configured to include an interconnected network of disparate textiles on which one or more users may interact with in the course of occupying that space.

Reference is made to FIG. 5, which illustrates a block diagram of a computing device 500, in accordance with an embodiment of the present application. As an example, the computing device 160 of FIG. 1 or the workspace data device 260 of FIG. 2 may be implemented using the example computing device 500 of FIG. 5. In some embodiments, the computing device 500 may be associated with a disparate textile and may be configured to transmit sensory data or other data signals to the workspace data device 260 of a workspace system.

The computing device 500 includes at least one processor 502, memory 504, at least one I/O interface 506, and at least one network communication interface 508.

The processor 502 may be a microprocessor or microcontroller, a digital signal processing (DSP) processor, an integrated circuit, a field programmable gate array (FPGA), a reconfigurable processor, a programmable read-only memory (PROM), or combinations thereof.

The memory 504 may include a computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM).

The I/O interface 506 may enable the computing device 500 to interconnect with one or more input devices, such as a keyboard, mouse, camera, touch screen and a microphone, or with one or more output devices such as a display screen and a speaker.

The networking interface 508 may be configured to receive sensory data or transmit actuating signals. In some examples, the received sensory data may be stored at the computing device 500.

In some embodiments, there may be processor-executable instructions or software that, when executed, by a processor converts the computing device 500 into a special purpose computing device to perform particular operations pursuant to instructions of the processor-executable instructions.

Although the embodiments have been described in detail, it should be understood that various changes, substitutions and alterations can be made herein without departing from the scope. Moreover, the scope of the present application is not intended to be limited to the particular embodiments of the process, machine, manufacture, composition of matter, means, methods and steps described in the specification.

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

The description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

As can be understood, the examples described above and illustrated are intended to be exemplary only.

What is claimed is:

1. A workspace system comprising:
   an electrical interconnection bus;
   a plurality of disparate textiles respectively coupled to the electrical interconnection bus, the respective disparate textiles having incorporated thereon a textile structure providing at least one of a sensor or an actuator, and wherein the disparate textiles are respectively associated with a workspace surface, and wherein said workspace surface includes a floor textile, said floor textile comprising a plurality of pressure sensing structures; and
   a computing device including a processor, a memory coupled to the processor, and a communication circuit coupled to the processor, wherein the computing device is coupled to the electrical interconnection bus to receive sensor data from at least one of the plurality of disparate textiles,
   wherein said computing device is configured to determine user occupancy or user traffic patterns within a workspace based on sensing data received from said floor textile, and
   wherein said workspace surface includes a space division textile, wherein said space division textile includes sound absorbing materials including acoustic foam and/or acoustic cones, said sound absorbing materials including shape shifting materials configured to change shape in response to an actuator signal to increase sound absorbing capacity, and
   wherein said computing device is configured to determine that said workspace is occupied based on sensing data received from said plurality of disparate textiles and, in response to determining that said workspace is occupied transmit the actuator signal to configure said sound absorbing materials to be reconfigured to include one or more of the acoustic cones protruding from said space division textile for dampening acoustic noise.

2. The workspace system of claim 1, wherein the workspace surface includes at least one of a tabletop textile, the space division textile, or a seating textile.

3. The workspace system of claim 1, wherein the workspace surface is a non-garment textile.

4. The workspace system of claim 1, wherein the textile structure includes at least one of an electrical, mechanical, or electro-mechanical structure.

5. The workspace system of claim 1, wherein the respective plurality of disparate textiles include at least one of shape shifting alloy yarn, thermal yarn, piezoelectric yarn, electromagnetic yarn, or electrical stimulation fiber.

6. The workspace system of claim 1, wherein the respective disparate textiles includes one or more fibers configured as the sensor to detect a physiological parameter of a user interacting with a respective disparate textile.

7. The workspace system of claim 1, wherein the electrical interconnection bus is a bi-directional interconnection bus configured to conduct at least one of a power or data signal to at least one of the plurality of disparate textiles.

8. The workspace system of claim 1, wherein the electrical interconnection bus includes an inductive charging circuit to provide power to at least one of the plurality of disparate textiles.

9. The workspace system of claim 1, comprising a power transformer configured to transform power signals for at least one of the plurality of disparate textiles.

10. The workspace system of claim 1, wherein the electrical interconnection bus includes at least one of a wired or wireless interconnection bus.

11. The workspace system of claim 1, wherein each of the plurality of disparate textiles includes one or more fibres configured as the actuator to provide feedback to a user based on the received sensor data from the at least one of the plurality of disparate textiles.

12. The workspace system of claim 1, wherein said computing device is configured to detect a gait of a user based on said data received from said floor textile.

13. The workspace system of claim 12, wherein said computing device is configured to determine an identity of the user based on said detected gait.

14. The workspace system of claim 1, wherein said actuator signal is a pulse-width modulated signal and/or an amplitude modulated signal associated with a range of acoustic cone shapes or depths.

* * * * *